(12) United States Patent
Kogure

(10) Patent No.: US 6,597,980 B2
(45) Date of Patent: Jul. 22, 2003

(54) ROAD FRICTION COEFFICIENTS ESTIMATING APPARATUS FOR VEHICLE

(75) Inventor: Masaru Kogure, Tokyo (JP)

(73) Assignee: Fuji Jukogyo Kabushiki Kaisha, Tokyo (JP)

(*) Notice: Subject to any disclaimer, the term of this patent is extended or adjusted under 35 U.S.C. 154(b) by 0 days.

(21) Appl. No.: 09/983,780

(22) Filed: Oct. 25, 2001

(65) Prior Publication Data

US 2002/0072841 A1 Jun. 13, 2002

(30) Foreign Application Priority Data

Oct. 26, 2000 (JP) ........................... 2000-327488

(51) Int. Cl.$^7$ ................ B60T 8/00; B60T 8/72
(52) U.S. Cl. ............. 701/80; 701/70; 303/160
(58) Field of Search ............... 701/70, 72, 75, 701/79, 80; 303/160, 155, 171, 150, 140; 180/197

(56) References Cited

U.S. PATENT DOCUMENTS

| | | | | |
|---|---|---|---|---|
| 5,351,192 A | * | 9/1994 | Tsuyama et al. | 364/426.03 |
| 5,944,392 A | * | 8/1999 | Tachihata et al. | 303/112 |
| 6,062,659 A | * | 5/2000 | Matsuda | 303/160 |
| 6,208,927 B1 | * | 3/2001 | Mine et al. | 701/70 |
| 6,401,023 B1 | * | 6/2002 | Takahashi | 701/70 |

FOREIGN PATENT DOCUMENTS

| | | |
|---|---|---|
| DE | 37 35 673 A1 | 5/1989 |
| EP | 0 412 791 A2 | 2/1991 |
| JP | 3-500866 | 2/1991 |
| JP | 08-002274 | 1/1996 |
| JP | 08-156627 | 6/1996 |
| JP | 10-242030 | 9/1998 |
| JP | 11-147460 | 6/1999 |
| JP | 2000-071968 | 3/2000 |
| JP | 2001-43352 | 2/2001 |

OTHER PUBLICATIONS

European Search Report dated Jan. 28, 2002.

* cited by examiner

Primary Examiner—Tan Q. Nguyen
Assistant Examiner—Dalena Tran
(74) Attorney, Agent, or Firm—McGinn & Gibb, PLLC (57) ABSTRACT

A road friction coefficients estimating apparatus for a vehicle comprises a first road friction coefficient estimating section for calculating a first road friction coefficient based on a vehicle behavior in a lateral direction, a second road friction coefficient estimating section for calculating a second road friction coefficient based on a vehicle behavior in a longitudinal direction, a third road friction coefficient estimating section for calculating a third road friction coefficient based on road conditions and an estimating value selection section for selecting either one of the first, second and third road friction coefficients as a final road friction coefficient estimating value.

20 Claims, 5 Drawing Sheets

ROAD FRICTION COEFFICIENTS ESTIMATING APPARATUS FOR VEHICLE

BACKGROUND OF THE INVENTION

1. Field of the Invention

The present invention relates to a road friction coefficients estimating apparatus for a vehicle for estimating friction coefficients on road surfaces and more particularly to a road friction coefficients estimating apparatus for accurately estimating friction coefficients on road surfaces over a wide range of vehicle motion.

2. Discussion of Prior Arts

In recent years, numerous vehicle control technologies such as a traction control technology, a braking force control technology, a torque distribution control technology and the like, have been proposed and some of these control technologies have been realized in actual automobile markets. Many of these control technologies use friction coefficients on a road surface (hereinafter, referred to as "road friction coefficient") for calculation or correction of control parameters. Accordingly, in order to execute the control properly, it is necessary to estimate an accurate road friction coefficient.

There are several technologies in which road friction coefficients are estimated. According to some technologies, road friction coefficients are estimated based on the comparison between an actual vehicle motion obtained from sensor inputs and a vehicle behavior obtained from a vehicle motion model. For example, the applicant of the present invention proposes a technology in which road friction coefficients are estimated by utilizing the adaptive control in Japanese Patent Application Laid-open No. Toku-Kai-Hei 8-2274. Also, the applicant of the present invention proposes a technology in which road friction coefficients are estimated based on the comparison of a slip angle of a vehicle estimated from an observer with a reference value on an road surface with high friction coefficient or an road surface with low friction coefficient respectively in Japanese Patent Application Toku-Gan-Hei 10-242030.

The technology in which road friction coefficients are estimated using a vehicle motion model is formed on the premise that the actual vehicle motion obtained from sensor inputs agrees with the behavior of the vehicle motion model under a specified condition (friction coefficient between tire and road surface is the same).

However, it is difficult to make the actual vehicle motion and the behavior of the vehicle motion model completely agree because of noises contained in the sensor inputs and errors in numerically modeling the vehicle. That is, these noises and errors produce the difference from an actual road friction coefficient.

Accordingly, in case of the technology in which road friction coefficients are estimated using vehicle motion models, it is desirable that road friction coefficients are estimated when the difference of road friction coefficients is substantially noticeable in the vehicle motion, compared to the effects of noises of sensor inputs and errors in modeling vehicle motions. Hence, it is difficult to estimate road friction coefficients accurately over a wide range of vehicle motion.

SUMMARY OF THE INVENTION

It is an object of the present invention to provide a road friction coefficients estimating apparatus capable of accurately estimating road friction coefficients over a wide range of vehicle motion.

In order to achieve the object, the road friction coefficients estimating apparatus for a vehicle comprises a first road friction coefficient estimating means for calculating a first road friction coefficient based on a vehicle behavior in a lateral direction, a second road friction coefficient estimating means for calculating a second road friction coefficient based on a vehicle behavior in a longitudinal direction, a third road friction coefficient estimating means for calculating a third road friction coefficient based on road conditions and an estimating value selection means for selecting either one of the first, second and third road friction coefficients as a final road friction coefficient estimating value.

DETAILED DESCRIPTION OF PREFERRED EMBODIMENTS

Figure 1:
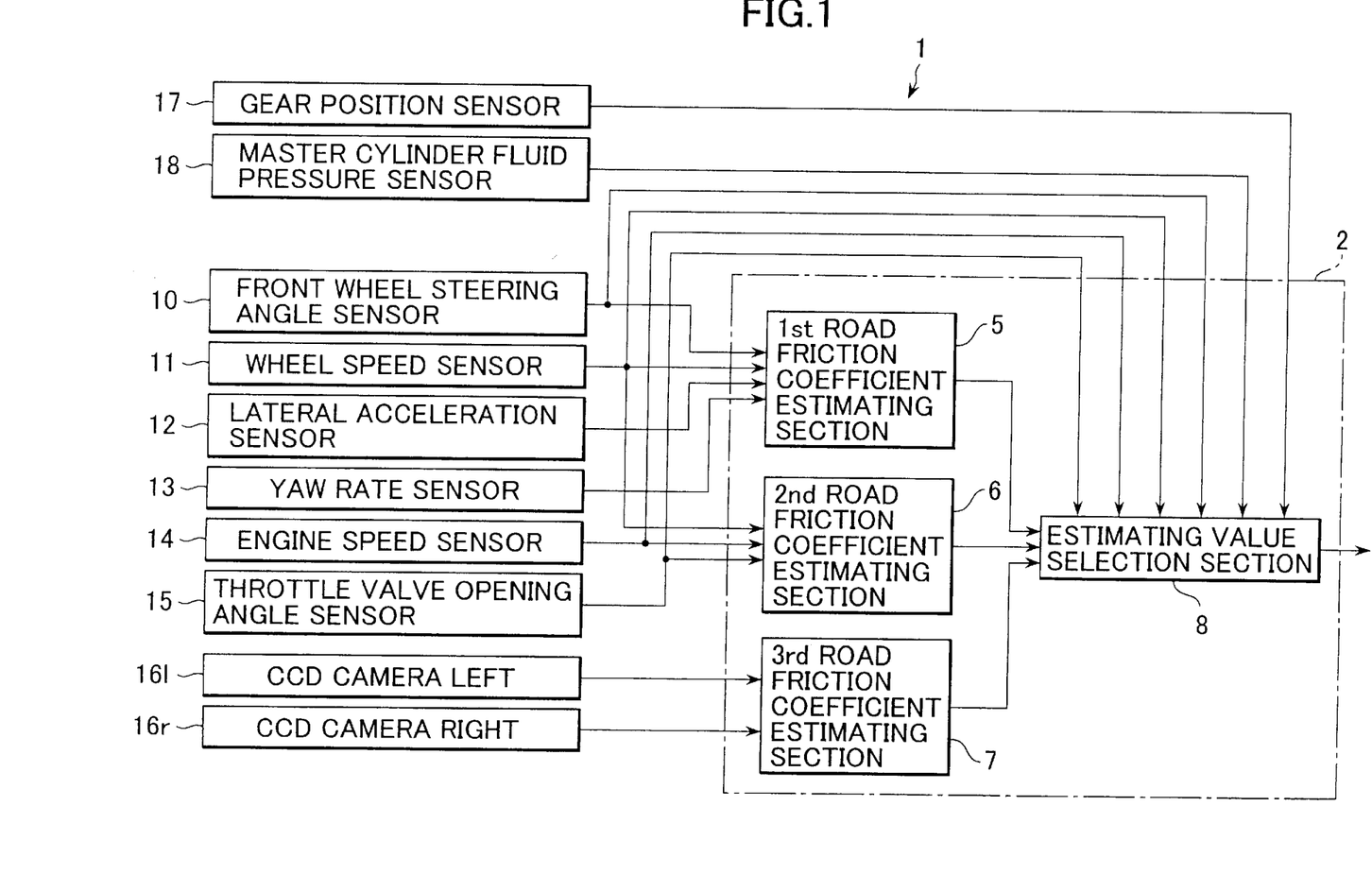
FIG. 1 is a functional block diagram showing a road friction coefficients estimating apparatus according to an embodiment of the present invention.

Referring now to FIG. 1, reference numeral 1 denotes a road friction coefficient estimating apparatus to be installed on a vehicle. Reference numeral 2 denotes a control section of the road friction coefficient estimating apparatus 1. The control section 2 comprises a first road friction coefficient estimating section 5 as a first road friction coefficient estimating means for calculating a first road friction coefficient estimating value $\mu_y$ based on a vehicle motion in a lateral direction, a second road friction coefficient estimating section 6 as a second road friction coefficient estimating means for calculating a second road friction coefficient estimating value $\mu_x$ based on a vehicle motion in a longitudinal direction, a third road friction coefficient estimating section 7 as a third road friction coefficient estimating means for calculating a third road friction coefficient estimating value $\mu_i$ based on road surface conditions and an estimating value selection section 8 for selecting a most reliable value from among the road friction coefficients $\mu_x, \mu_y, \mu_i$ estimated in the first, second and third road friction coefficient estimating sections 5, 6 and 7 and outputting the value as a final road friction coefficient estimating value $\mu_{out}$.

The first road friction coefficient estimating section 5 is connected with a front wheel steering angle sensor 10, a wheel speed sensor 11, a lateral acceleration sensor 12 and a yaw rate sensor 13 and inputs a front wheel steering angle $\delta_f$, respective wheel speeds $V_{fl}$, $V_{fr}$, $V_{rl}$, $V_{rr}$, a lateral acceleration $d^2y/dt^2$, a yaw rate $d\phi/dt$ from respective sensors. In the first road friction coefficient estimating section 5, the first road friction coefficient estimating value $\mu_y$ is obtained by using the adaptive control theory which the applicant of the present invention discloses in Japanese Patent Application Laid-open No. 8-2274, that is, the first road friction coefficient estimating value $\mu_y$ is obtained based on the ratio of an equivalent cornering power of front wheels to that of rear wheels on an road surface having high friction coefficient according to the equation of vehicle motion in the lateral direction using a front wheel steering angle $\delta_f$, a vehicle speed V, a lateral acceleration $d^2y/dt^2$, a yaw rate $d\phi/dt$ by extending the cornering powers of the front and rear wheels to a non-linear region. Specifically, the first road friction coefficient estimating value $\mu_y$ is calculated according the following adaptive control theory on the basis of the parameter adjustment rule.

Figure 2:
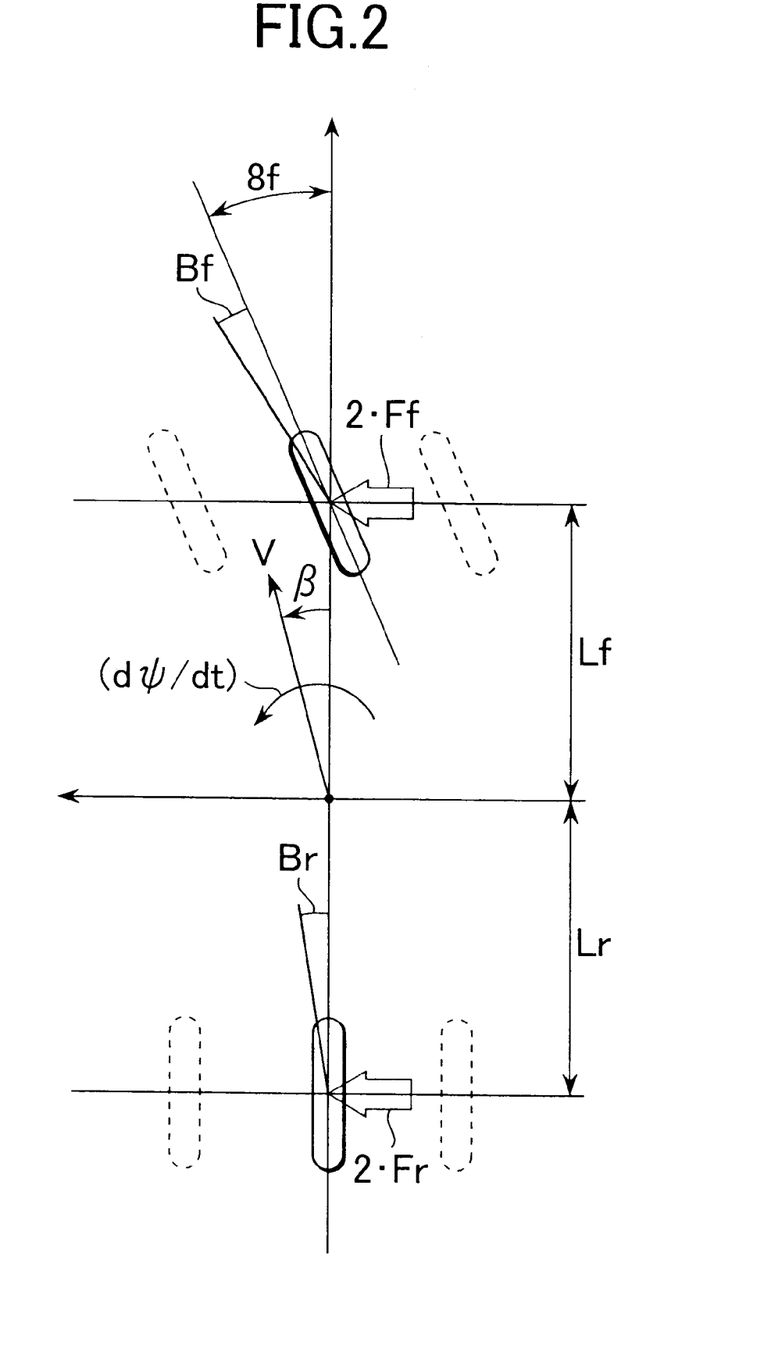
FIG. 2 is a diagram showing a two wheel vehicle model equivalent to a four wheel vehicle.

The equation of lateral transitional motion of a vehicle is expressed using a vehicle motion model illustrated in FIG. 2 as:

$$M \cdot (d^2y/dt^2) = 2 \cdot F_f + 2 \cdot F_r \qquad (1)$$

where M is mass of a vehicle; $F_f$, $F_r$ are cornering forces of front and rear wheels, respectively; and $d^2y/dt^2$ is lateral acceleration.

On the other hand, the equation of rotational motion around gravity center of the vehicle is expressed as:

$$I_z \cdot (d^2\phi/dt^2) = 2 \cdot F_f L_f - 2 \cdot F_r \cdot L_r \qquad (2)$$

where $I_z$ is yaw moment of inertia of the vehicle; $L_f$, $L_r$ are distances from the center of gravity to the front and rear wheels, respectively; and $(d^2\phi/dt^2)$ is yaw angular acceleration.

The lateral acceleration $(d^2y/dt^2)$ is expressed as:

$$(d^2y/dt^2) = V \cdot ((d\beta/dt) + (d\phi/dt)) \qquad (3)$$

where V is vehicle speed; $\beta$ is slip angle of the vehicle; and $(d\beta/dt)$ is slip angular velocity of the vehicle.

The cornering forces have a response similar to a first-order time lag. In this case, this time lag being neglected and letting the cornering forces be linearized introducing an idea of equivalent cornering power in which suspension characteristic is involved in tire characteristic, the cornering forces are expressed as follows:

$$F_f = -K_f \beta_f \qquad (4)$$

$$F_r = -K_r \beta_r \qquad (5)$$

where $K_f$, $K_r$ are equivalent cornering powers of front and rear wheels, respectively; and $\beta_f$, $\beta r_f$ are lateral slip angles of front and rear wheels, respectively.

Using equivalent cornering powers taking the effect of roll and suspension of the vehicle into consideration, lateral slip angles $\beta_f$, $\beta_r$ are can be simplified as follows:

$$\beta_f = \beta + L_f (d\phi/dt)/V - \delta_f \qquad (6)$$

$$\beta_r = \beta - L_r \cdot (d\phi/dt)/V \qquad (7)$$

where $\delta_f$ is steering angle of front wheel.

Various parameters are estimated by expressing the aforesaid equation of motion in state variables and applying the adaptive control theory to the equation according to the parameter adjustment rule. Next, cornering powers of the vehicle are obtained from the parameters thus estimated. There are many parameters for the vehicle such as vehicle mass, yaw inertia moment and the like. In the present invention, these parameters are assumed to be constant. Only cornering powers of tire are assumed to change. There are some reasons why the cornering powers of tire change,
a non-linearity of lateral force versus slip angle, an effect of road friction coefficients, an effect of load transference and the like. The cornering powers $K_f$, $K_r$ of front and rear wheels are obtained from the following equations:

$$K_f = (q \cdot I_z \cdot n)/(2 \cdot L_f) \qquad (8)$$

$$K_r = (p \cdot I_z + L_f K_f)/L_r \qquad (9)$$

where p is a parameter estimated from a change of yaw rate; and q is a parameter estimated from a front wheel steering angle $\delta_f$.

Accordingly, the cornering powers $K_f$, $K_r$ of front and rear wheels are estimated according to the equations (8), (9) in an extended non-linear area.

Further, road friction coefficient estimating values $E_f$, $E_r$ of front and rear wheels respectively are expressed as:

$$E_f = K_f/K_{f0} \qquad (10)$$

$$E_r = K_r/K_{r0} \qquad (11)$$

The first road friction coefficient estimating value $\mu_y$ is calculated by averaging these road friction coefficient estimating values $E_f$, $E_r$.

As clearly understood from the above formulas, the method of thus estimating road friction coefficients based on vehicle behaviors in the lateral direction provides more accurate estimating values in case where a relatively large steering input is applied to the vehicle.

Figure 3:
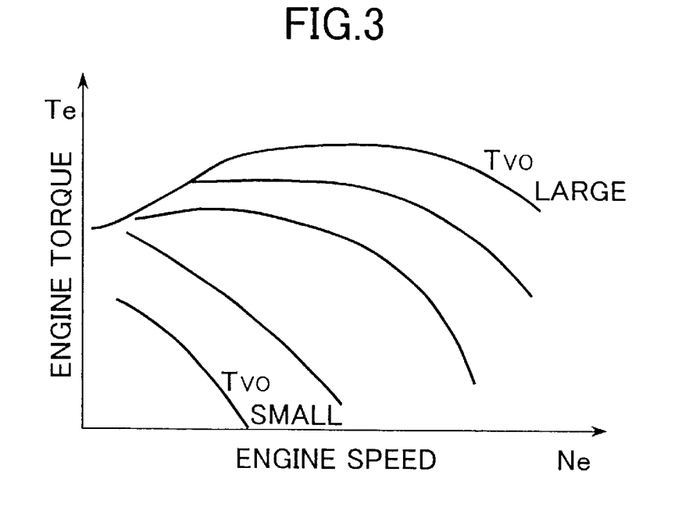
FIG. 3 is a schematic diagram showing a table of engine torque versus engine speeds in respective throttle valve opening angles.

The second road friction coefficient estimating section 6 is connected with the wheel speed sensors 11 for respective four wheels, an engine speed sensor 14 and a throttle valve opening angle sensor 15 and inputs wheel speeds $V_{rl}$, $V_{rr}$, engine speed $N_e$ and throttle opening angle $T_{vo}$, respectively. In the second road friction coefficient estimating section 6, road friction coefficient estimating values $\mu_{rl}$, $\mu_{rr}$ for left and right rear drive wheels respectively are calculated according to the method disclosed in Japanese Patent Application No. Toku-Hyo-Hei 3-500866 for example using wheel speeds $V_{rl}$, $V_{rr}$ for left and right rear drive wheels respectively and engine torque $T_e$ and a second road friction coefficient estimating value $\mu_x$ is obtained from the road friction coefficient estimating values $\mu_{rl}$, $\mu_{rr}$. Engine torque $T_e$ is estimated from a table shown in FIG. 3 based on engine speed $N_e$ and throttle valve opening angle $T_{vo}$.

How to calculate the road friction coefficient estimating value $\mu_{rl}$ of the left rear left wheel is exemplified below.

First, parameters for the rear left wheel $P_{11}$, $P_{21}$ and $C_1$ are estimated from the following formula.

$$V_{rl}(K+1) = P_{21} \cdot V_{rl}(K) + P_{11} \cdot T_e(K) + C_1 \qquad (12)$$

where $V_{rl}(K+1)$ is a wheel speed obtained at time $(K+1) \cdot t_a$; $V_{rl}(K)$ is a wheel speed obtained at time $K \cdot t_a$; $T_e(K)$ is an engine torque obtained at time $K \cdot t_a$; $t_a$ is clock time of the computer and K is step number.

Based on thus obtained parameters, the road friction coefficient estimating value $\mu_{rl}$ is obtained by the following formulas:

$$\mu_{rl} = -K_{21} \cdot (Z_1 - V'_{rl}) + (C_{THrl}/(F_{ZHstat} \cdot r_R)) \qquad (13)$$

$$K_{21} = ((I_{rl} \cdot V_0)/(F_{ZHstat} \cdot r_R^2)) \cdot ((lnP_{21})/t) \qquad (14)$$

$$Z_1 = C_1/(1 - P_{21}) \qquad (15)$$

$$C_{Thrl} = -I_{r2} \cdot (\omega_{rr} - \omega_{rl}) \qquad (16)$$

Where $I_{r1}$, $I_{r2}$ are constants determined by inertia moment of gear; $V_0$ is a constant presenting a reference value when normalizing wheel speed; $V'_{rl}$ is wheel speed $V_{rl}$ normalized at $V_0$; $F_{Zhstat}$ is static load on wheel; $r_R$ is radius of wheel and $\omega_{rr}$, $\omega_{rl}$ are angular velocity of wheel.

As clearly understood from the above formulas, the method of thus estimating road friction coefficients based on vehicle behaviors in the longitudinal direction provides more accurate estimating values in case where relatively large braking and driving forces are applied to the vehicle.

The third road friction coefficient estimating section 7 is connected with a pair of left and right CCD cameras 16$_l$, 16$_r$, and inputs mages of the scenery in front of the vehicle through these cameras. In the third friction coefficient estimating section 7, it is judged based on image data from the left and right CCD cameras whether or not the road on which the vehicle presently travels is in any situations of snowy, wet and dry conditions and the third road friction coefficient estimating value $\mu_i$ is obtained based on thus obtained road situation.

That is, as the applicant of the present invention describes in detail in Japanese Patent Application Laid-open No. Toku-Gan-Hei 11-216191 for example, the judgment of snowy road in the third road friction coefficient estimating section 7 is made based on image data in a designated observing area in the images taken by the left and right CCD cameras 16$_l$, 16$_r$ by detecting a road condition in which the road is regarded as to be covered with snow overall. Specifically, the number of brightness edges in the horizontal direction of the observing area and an overall size of brightness edges in the observing area are calculated respectively. In case where the number of brightness edges is smaller than a threshold value and further the overall size of brightness, it is judged that the road is regarded as a snowy road covered with snow overall.

Further, the judgment of asphalted wet road in the third friction coefficient estimating section 7 is made by the method which the applicant of the present invention describes in Japanese Patent Application Unexamined No. Toku-Gan-Hei 11-216713. Specifically, first a distant data observing area is established in the frontal area of the vehicle where a road is supposed to exist and a hightwise distribution is evaluated with respect to the distance data existing in the observing area. That is, obtaining the height of the calculated distance data in a three dimensional space, the number of distance data of solid objects in the road surface is counted as the number of wet data. The asphalted wet road has a characteristic that many distance data are calculated below the road surface level. In consideration of this characteristic, in case where there are substantially many wet data in the distance data observing area, the road surface is judged to be in a wet condition.

Further, in the third road friction coefficient estimating section 7, the road friction coefficient estimating value $\mu_i$ is established as follows:

on snowy road $\mu_i=0.3$
on asphalted wet road $\mu_i=0.7$
on asphalted dry road $\mu_i=0.9$ The estimating value selection section 8 is connected with the front wheel steering angle sensor 10, the wheel speed sensor 11, the engine speed sensor 14, the throttle valve opening angle sensor 15, a gear position sensor 17 and a fluid pressure sensor 18 of a master cylinder and inputs front wheel steering angle $\delta_f$, respective wheel speeds $V_{fl}$, $V_{fr}$, $V_{rl}$, $V_{rr}$, engine speed $N_e$, throttle valve opening angle $T_{vo}$, gear position $G_p$ and fluid pressure $P_{mc}$ of the master cylinder. Further, the estimating value selection section 8 is connected with the first, second and third road friction coefficient estimating section 5, 6 and 7 respectively and inputs the first, second and third road friction coefficient estimating values $\mu_v$, $\mu_x$ and $\mu_i$. Further, the estimating value selection section 8 calculates a longitudinal force (braking force and driving force) $F_x$ exerted on the wheels and a lateral force $F_y$ exerted on wheels based on the aforesaid sensor values and calculated estimating values and determines a final road friction coefficient estimating value $\mu_{out}$ based on these $F_x$, $F_y$.

Figure 7:
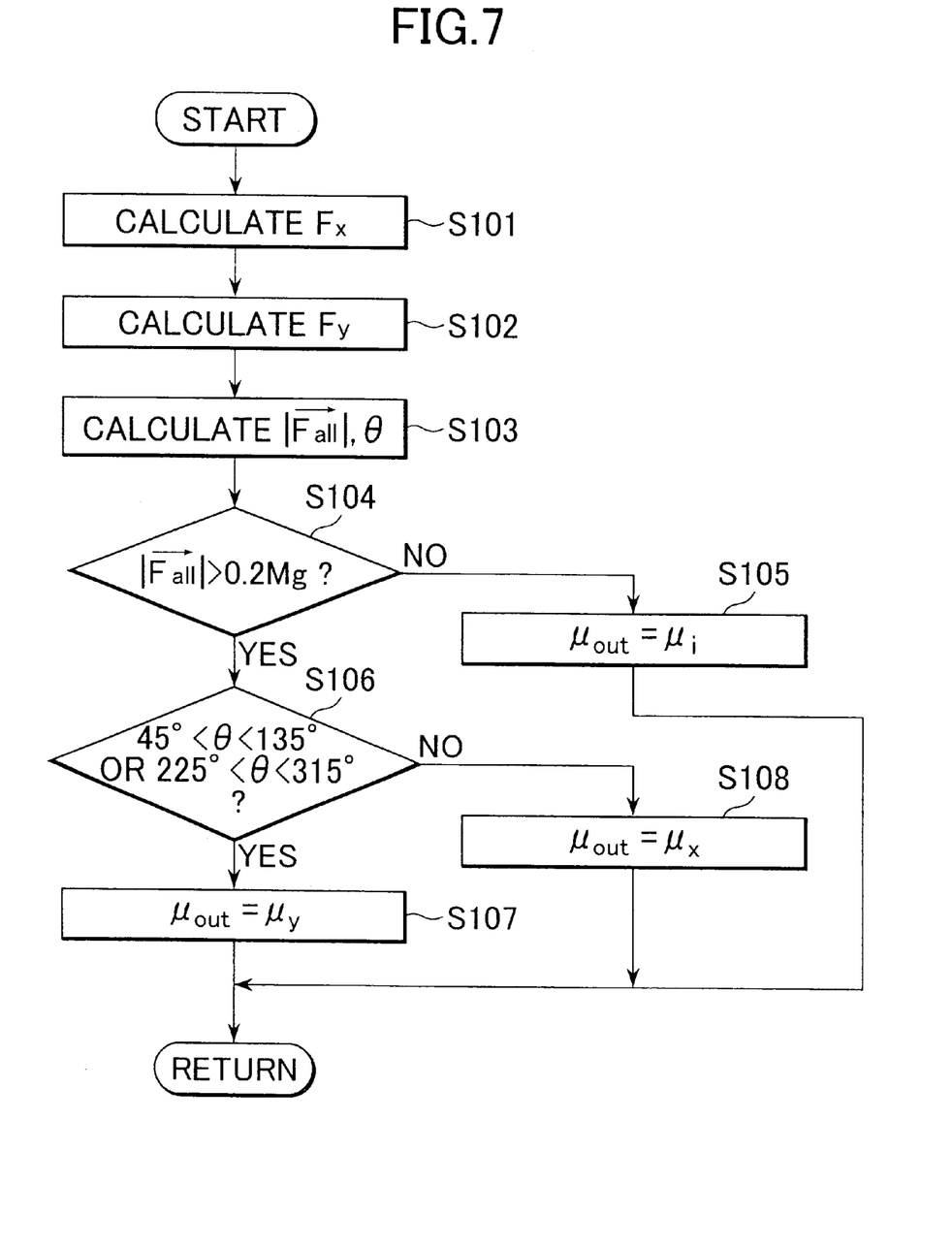
FIG. 7 is a flowchart showing a routine for selecting estimating value.

Below, processes of the estimating value selection section 8 will be described in detail by reference to a flowchart of an estimating value selection routine shown in FIG. 7.

This routine is executed at a specified time interval. At a step S101, first braking and driving force $F_x(=F_f+F_e)$ exerted on wheels is calculated, assuming that the road on which presently the vehicle travels has a reference road surface (flat road surface with road friction coefficient=1).

A total braking force $F_f$ exerted on wheels is obtained by the following formula:

$$F_f = -2 \cdot (F_{Ft} + F_{Rr}) \tag{17}$$

where $F_{Ft}$ is braking force exerted on a front wheel; and $F_{Rr}$ is braking force exerted on a rear wheel. Further, $F_{Ft}$ and $F_{Rr}$ are expressed as follows:

$$F_{Ft} = ((\pi \cdot Dwc^2)/4) \cdot P_{Ft} \cdot C_{Ft} \cdot (R_{b\_Ft}/R_w) \tag{18}$$

$$F_{Rr} = ((\pi \cdot Dwc^2)/4) \cdot P_{Rr} \cdot C_{Rr} \cdot (R_{b\_Rr}/R_w) \tag{19}$$

where $P_{Ft}$, $P_{Rr}$ are brake fluid pressure for front and rear wheel respectively; $D_{wc}$ is inner diameter of a wheel cylinder; $C_{Ft}$, $C_{Rr}$ are brake factors for front and rear wheel respectively; $R_{b\_Ft}$, $R_{b\_Rr}$ are effective radius of brake rotor for front and rear wheel respectively; and $R_w$ is effective radius of tire.

Figure 4:
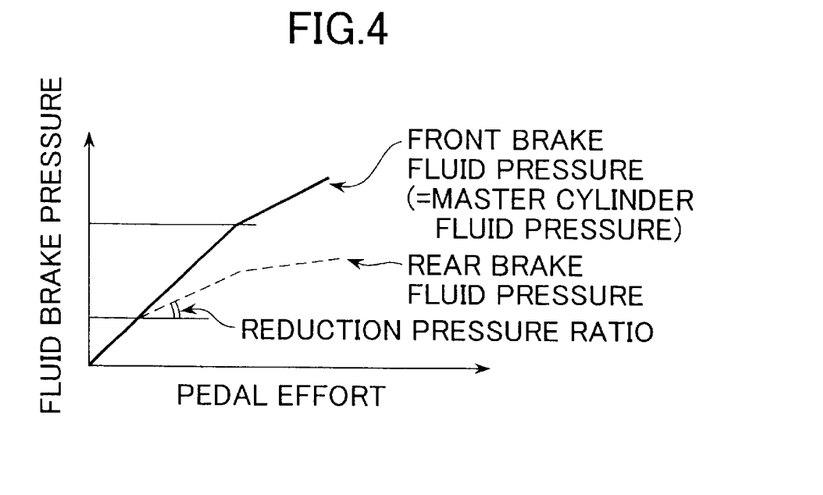
FIG. 4 is schematic diagram showing a table of brake pressure versus brake pedal depressing effort.

Brake fluid pressures $P_{ft}$, $P_{Rr}$ are obtained from a table (see FIG. 4) stored in the estimating value selection section 8 based on master cylinder fluid pressure $P_{mc}$. In this case, front wheel brake fluid pressure $P_{Ft}$ is established so as to coincide with master cylinder fluid pressure $P_{mc}$ and rear wheel brake fluid pressure $P_{Rr}$ is established so as to be reduced at a specified reduction pressure ratio from master cylinder fluid pressure $P_{mc}$.

Driving force $F_e$ exerted on the wheels is obtained by the following formula:

$$F_e = T_t \cdot \text{fin}/r_t \tag{20}$$

where $T_t$ is torque of an output shaft of a transmission; fin is final reduction gear ratio; and $r_t$ is tire radius.

The transmission output torque $T_t$ is obtained from the following formula:

$$T_t = T_e \cdot gr \cdot t_{\_conv} \cdot \eta \tag{21}$$

where Te is engine torque; gr is gear ratio of the transmission; $t_{\_conv}$ is torque ratio; and $\eta$ is power transmission efficiency.

The engine torque $T_e$ is obtained from a table (see FIG. 3) parameterizing engine speed $N_e$ and throttle valve opening angle $T_{vo}$ and the transmission gear ratio gr is determined based on a gear position $G_p$ inputted.

Next, at a step S102, lateral force $F_y$ exerted on wheels is calculated, assuming that the road on which presently the vehicle travels has a reference road surface (flat road surface with road friction coefficient=1). Specifically, at the step S102, a high friction coefficient ($\mu=1$) or reference road based lateral acceleration $(d^2y/dt^2)_H$ is estimated from an equation of state which will be described after and a lateral force $F_y$ exerted on the wheels is calculated by multiplying the reference road based lateral acceleration $(d^2y/dt^2)_H$ by vehicle mass M.

In this case, the reference road based lateral acceleration $(d^2y/dt^2)_H$ is calculated from the following equation of state which is described in detail in Japanese Patent Application No. Toku-Gan-Hei 11-266216 filed by the applicant of the present invention.

$$(dx(t)/dt) = A \cdot x(t) + B \cdot u(t)$$

$$x(t) = [\beta (d\phi/dt)]^T$$

$$u(t) = [\delta_f \rho]^T$$

$$A = \begin{bmatrix} a_{11} & a_{12} \\ a_{21} & a_{22} \end{bmatrix}$$

$$B = \begin{bmatrix} b_{11} & b_{12} \\ b_{21} & b_{22} \end{bmatrix}$$

$$a_{11} = -2 \cdot (K_f + K_r)/(M \cdot V)$$

$$a_{12} = -1 - 2 \cdot (L_f K_f - L_r \cdot K_r)/(M \cdot V^2)$$

$$a_{21} = -2 \cdot (L_f K_f - L_r \cdot K_r)/I_z$$

$$a_{22} = -2 \cdot (L_f^2 \cdot K_f + L_r^2 \cdot K_r)/(I_z \cdot V)$$

$$b_{11} = 2 \cdot K_f/(M \cdot V)$$

$$b_{21} = 2 \cdot L_f K_f/I_z$$

$$b_{12} = b_{22} = 0 \tag{22}$$

In the estimating value selection section 8, a reference road based slip angular velocity $(d\beta/dt)_H$ and a refernce road based yaw angular acceleration $(d^2\phi/dt^2)_H$ are obtained by calculating $(dx(t)/dt) = [(d\beta/dt)(d^2\phi/dt^2)]^T$ in a vehicle operating condition (vehicle speed V, front wheel steering angle $\delta_f$), when equivalent cornering powers $K_f$, $K_r$ at 1.0 for example of road friction coefficient have been established beforehand in the formula (22). Then, a reference road based vehicle slip angle $\beta_H$ and a reference road based yaw rate $(d\phi/dt)_H$ are obtained by integrating the vehicle slip angular velocity $(d\beta/dt)_H$ and the yaw angular acceleration $(d^2\phi/dt^2)_H$. Further, a reference road based front wheel slip angle $\beta_{fH}$ is calculated by substituting the reference road based slip angle $\beta_H$ and yaw rate $(d\phi/dt)_H$ into the aforesaid formula (6). Further, a reference road based lateral acceleration $(d^2y/dt^2)_H$ is calculated by substituting the reference road based vehicle slip angular velocity $(d\beta/dt)_H$ and yaw rate $(d\phi/dt)_H$ into the aforesaid formula (3).

Figure 5:
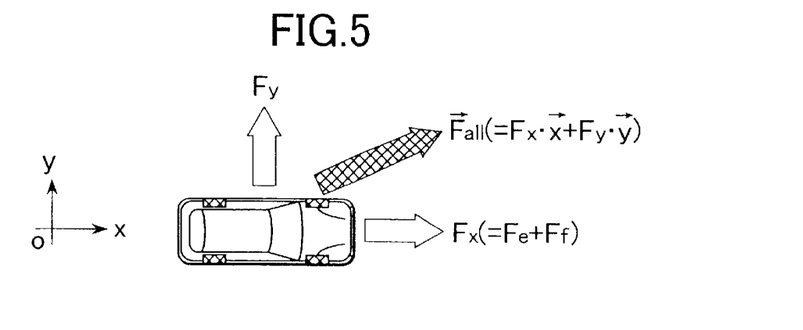
FIG. 5 is an explanatory view showing forces exerted on wheels.
Figure 6:
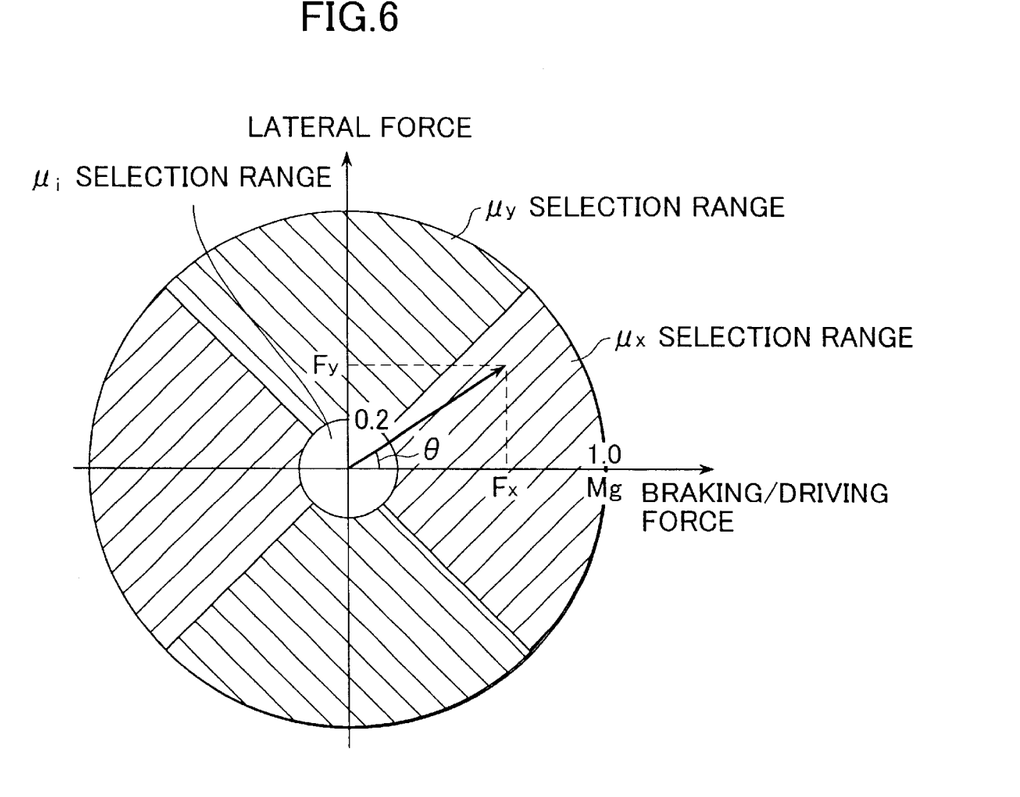
FIG. 6 is an explanatory view showing an estimating value selection friction circle.

Next, at a step S103, as shown in FIG. 5, a resultant force $F_{all,ve}$ of a braking/driving force $F_{x,ve}$ and a lateral force $F_{y,ve}$ is obtained by calculating a magnitude of the resultant force $|F_{all,ve}|$ of the braking/driving force $F_{x,ve}$ and the lateral force $F_{y,ve}$ and an angle $\theta$ contained by the resultant force and x axis. Symbols having a subscript "$_{ve}$" denote values expressed in vector.

That is, the resultant force $F_{all,ve}$ of the braking/driving force $F_{x,ve}$ and the lateral force $F_{y,ve}$ is obtained by the following formulas:

$$F_{all,ve} = |F_{all,ve}| \cdot \tan \theta \tag{23}$$

$$|F_{all,ve}| = (F_x^2 + F_y^2)^{1/2} \tag{24}$$

$$\theta = \tan^{-1}(F_y/F_x) \tag{25}$$

Since friction coefficients between road surface and rubber obey the principle of Coulomb's friction, resultant horizontal forces ($F_{all,ve}$) exerted between respective wheels and road surface never exceed a product of friction coefficient $\mu$ and vertical load M·g (M: vehicle mass, g: gravitational acceleration). That is, the following relationship is formed:

$$(F_x^2 + F_y^2)^{1/2} \leq \mu \cdot M \cdot g \tag{26}$$

In the estimating value selection section 8, which road friction estimating values has a highest reliability of the first to third road friction coefficient estimating values $\mu_y$, $\mu_x$ and $\mu_i$ is selected by investigating the condition of the resultant force $F_{all,ve}$ exerted on wheels in a friction circle on the reference road surface (flat and road friction coefficient=1) in the processes of the following steps S104 to S108. Specifically, as shown in FIG. 5, selection areas of respective road friction coefficient estimating values $\mu_y$, $\mu_x$ and $\mu_i$ are established in a friction circle and a road friction coefficient estimating value is selected by investigating which area of those selected ones contains the resultant force $F_{all,ve}$.

When the program goes from the step S103 to a step S104, first, it is investigated whether or not the magnitude of the absolute vale $|F_{all,ve}|$ of the resultant force exerted on the wheel is larger than 0.2·M·g for example. That is, at the step S104, it is checked whether or not the vehicle indicates a behavior enough to estimate road friction coefficients from the vehicle behaviors in the lateral or longitudinal directions by investigating whether or not the absolute value $|F_{all,ve}|$ of the resultant force exerted on wheels is larger than a specified ratio (0.2·M·g) of the largest value $\mu \cdot M \cdot g$ (=M·g when $\mu$=1) which the absolute value can take.

Further, at the step S104, in case where the absolute value $|F_{all,ve}|$ of the resultant force exerted on wheels is smaller than 0.2·M·g, the program goes to a step S105 where a final road friction coefficient estimating value $\mu_{out}$ is established to $\mu_i$ based on the judgment that the vehicle behavior is not enough and the third road friction coefficient estimating value $\mu_i$ estimated from the road conditions is most reliable and after that leaves the routine.

On the other hand, at the step S104, in case where the absolute value $|F_{all,ve}|$ of the resultant force exerted on wheels is larger than 0.2·M·g, it is judged that either of the road friction coefficient estimating values $\mu_x$, $\mu_y$ which have been estimated from the vehicle behaviors in the lateral or longitudinal directions has a higher reliability than the third road friction coefficient estimating value $\mu_i$ which has been estimated from the road surface conditions and the program goes to a step S106.

At the step S106, it is checked whether or not the angle $\theta$ contained by the resultant force $F_{all,ve}$ and X axis is 45 degrees<$\theta$<135 degrees or 225 degrees<$\theta$<315 degrees. That is, it is checked whether or not the direction of the resultant force $F_{all,ve}$ is biased in the lateral direction.

In case where at the step S106 the resultant force $F_{all,ve}$ is 45 degrees<$\theta$<135 degrees or 225 degrees<$\theta$<315 degrees with respect to x axis, that is, in case where the direction of the resultant force $F_{all,ve}$ is biased in the lateral direction, after a final road friction coefficient estimating value $\mu_{out}$ is established to $\mu_y$ based on the judgment that the first road friction coefficient estimating value $\mu_y$ estimated from the vehicle behavior in the lateral direction is most reliable, the program leaves the routine.

On the other hand, in case where at the step S106 the resultant force $F_{all,ve}$ is in a range other than 45 degrees<$\theta$<135 degrees or 225 degrees<$\theta$<315 degrees with respect to x axis, that is, in case where the direction of the resultant force $F_{all,ve}$ is biased in the longitudinal direction, after a final road friction coefficient estimating value $\mu_{out}$ is established to $\mu_x$ based on the judgment that the second road friction coefficient estimating value $\mu_x$ estimated from the vehicle behavior in the longitudinal direction is most reliable, the program leaves the routine.

According to the embodiment described above, since the road friction coefficient is estimated based on the road conditions in addition to the vehicle behavior and a most reliable one is selected as a final road friction coefficient estimating value from a plurality of these estimated road friction coefficient estimating values, road friction coefficients can be estimated accurately in a wide range. Particularly, since the estimation of road friction coefficient based on the vehicle behavior is performed in two ways, one is based on the vehicle behavior in the lateral direction and the other is based on the vehicle behavior in the longitudinal direction and a most reliable one is selected from these road friction coefficients in two ways as a final road friction coefficient, the estimation accuracy of the road friction coefficients can be enhanced.

Further, a most reliable one is selected as a final road friction coefficient estimating value based on the resultant force exerted on the wheel accurately by a simple process.

Specifically, according to the magnitude of the force exerted on the wheel, either the road friction coefficient estimating value based on the vehicle behaviors or the road friction coefficient estimating value based on the road surface conditions is selected. Further, according to the direction of the force exerted on the wheel, either the road friction coefficient estimating value based on the vehicle behavior in the lateral direction or the road friction coefficient estimating value based on the vehicle behavior in the longitudinal direction is selected. These selections enable to perform an accurate estimation of road friction coefficients.

While the presently preferred embodiment of the present invention has been shown and described, it is to be understood that this disclosure is for the purpose of illustration and that various changes and modifications may be made without departing from the scope of the invention as set forth in the appended claims.

What is claimed is:

1. A road friction coefficients estimating apparatus for a vehicle for estimating friction coefficients of road surfaces on which said vehicle travels, comprising:

a first road friction coefficient estimating means for calculating a first road friction coefficient based on a vehicle behavior in a lateral direction;

a second road friction coefficient estimating means for calculating a second road friction coefficient based on a vehicle behavior in a longitudinal direction;

a third road friction coefficient estimating means for calculating a third road friction coefficient based on road conditions, and an estimating value selection means for selecting either one of said first, second and third road friction coefficients as a final road friction coefficient estimating value according to a calculated force exerted on the wheels of the vehicle based upon a reference road surface having a constant friction coefficient.

2. The road friction coefficient estimating apparatus according to claim 1, wherein said calculated force is based upon a driver's control of said vehicle.

3. The road friction coefficient estimating apparatus according to claim 1, wherein said estimating value selection means selects said third road friction coefficient as a final road friction coefficient estimating value when the magnitude of said calculated force is smaller than a specified value.

4. The road friction coefficient estimating apparatus according to claim 1, wherein said estimating value selection means selects said first road friction coefficient as a final road friction coefficient estimating value when the magnitude of said calculated force is larger than a specified value and the direction of said calculated force is biased in a lateral direction.

5. The road friction coefficient estimating apparatus according to claim 1, wherein said estimating value selection means selects said second road friction coefficient as a final road friction coefficient estimating value when the magnitude of said calculated force is larger than a specified value and the direction of said calculated force is biased in a longitudinal direction.

6. The road friction coefficient estimating apparatus according to claim 1, wherein said third road friction coefficient estimating means detects road conditions from images taken by an imaging means.

7. The road friction coefficient estimating apparatus according to claim 6, wherein said imaging means is a stereoscopic picture imaging means and said images are a pair of images taken by said imaging means.

8. A road friction coefficient estimating apparatus for a vehicle for estimating friction coefficients for a road surface on which said vehicle travels, comprising:

a first road coefficient estimating section for calculating a first road friction coefficient based on a vehicle behavior in a lateral direction;

a second road coefficient estimating section for calculating a second road friction coefficient based on a vehicle behavior in a longitudinal direction;

a third road coefficient estimating section for calculating a third road friction coefficient based on a road condition; and an estimating value selection means for selecting one of said first, second and third road friction coefficients as a final road friction coefficient estimating value based upon a calculated resultant force, of a braking/driving force and a lateral force, exerted on wheels of said vehicle in a friction circle on a reference road surface having a flat and constant friction coefficient.

9. The apparatus of claim 8, wherein said estimating value selection means investigates selection areas of said first, second and third road coefficient estimating values established in said friction circle, and selects said final road friction coefficient estimating value by investigating which areas of those selected ones contains said calculated resultant force.

10. A road friction coefficient estimator that estimates a friction coefficient of a road surface on which a vehicle travels, comprising:

a lateral road friction coefficient estimator that calculates a lateral road friction coefficient based upon the behavior of the vehicle in a lateral direction;

a longitudinal road friction coefficient estimator that calculates a longitudinal road friction coefficient based upon the behavior of the vehicle in a longitudinal direction;

a road condition friction coefficient estimator that calculates a road condition friction coefficient based upon a road condition; and a selector that selects one of the lateral road friction coefficient, longitudinal road friction coefficient and the road condition friction coefficient as a final road friction coefficient based upon a calculated force which is based upon a constant road force coefficient from a reference road surface.

11. The estimator of claim 10, wherein the calculated force comprises a calculated resultant force that is based upon a lateral road friction coefficient and a longitudinal road friction coefficient which are both based upon said constant road force coefficient.

12. The estimator of claim 11, wherein the selector selects the road condition friction coefficient as the final road friction coefficient when the calculated resultant force is less than a specified value and selects one of the lateral road friction coefficient and the longitudinal road friction coefficient when the calculated resultant force is larger than the specified value.

13. The estimator of claim 12, wherein the specified value is based upon a mass (M) of the vehicle and gravity (g).

14. The estimator of claim 13, wherein the specified value is 0.2 (M×g).

15. The estimator of claim 12, wherein the selector selects the lateral road friction coefficient as the final road friction coefficient when the calculated resultant force is biased in the lateral direction.

16. The estimator of claim 12, wherein the selector selects the longitudinal road friction coefficient as the final road friction coefficient when the calculated resultant force is biased in the longitudinal direction.

17. The estimator of claim 10, wherein the road condition friction coefficient estimator comprises an imager that generates an image and wherein said road friction coefficient is based upon said image.

18. The estimator of claim 17, wherein the imager comprises a first charge coupled device (CCD) camera that generates a first image.

19. The estimator of claim 18, wherein the imager further comprises a second CCD camera that generates a second image and wherein the road condition friction coefficient estimator calculates a road condition friction coefficient based upon the first image and the second image.

20. The estimator of claim 19, wherein the first image and the second image form a stereoscopic image and wherein the road condition friction coefficient estimator calculates a road condition friction coefficient based upon the stereoscopic image.

* * * * *